(12) United States Patent
Alibek et al.

(10) Patent No.: US 12,344,883 B2
(45) Date of Patent: Jul. 1, 2025

(54) METHODS FOR PURIFICATION OF SOPHOROLIPIDS

(71) Applicant: Locus Solutions IPCo, LLC, Solon, OH (US)

(72) Inventors: Ken Alibek, Solon, OH (US); Sean Farmer, Ft. Lauderdale, FL (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 342 days.

(21) Appl. No.: 17/765,552

(22) PCT Filed: Dec. 18, 2020

(86) PCT No.: PCT/US2020/065855
§ 371 (c)(1),
(2) Date: Mar. 31, 2022

(87) PCT Pub. No.: WO2021/127339
PCT Pub. Date: Jun. 24, 2021

(65) Prior Publication Data
US 2022/0364136 A1    Nov. 17, 2022

Related U.S. Application Data

(60) Provisional application No. 62/993,158, filed on Mar. 23, 2020, provisional application No. 62/951,058, filed on Dec. 20, 2019.

(51) Int. Cl.
| | |
|---|---|
| C12P 19/44 | (2006.01) |
| C12N 1/16 | (2006.01) |
| C12N 9/04 | (2006.01) |
| C12N 13/00 | (2006.01) |
| C12P 7/6436 | (2022.01) |
| C12P 7/6481 | (2022.01) |

(52) U.S. Cl.
CPC .............. *C12P 7/6436* (2013.01); *C12N 1/16* (2013.01); *C12N 9/0006* (2013.01); *C12N 13/00* (2013.01); *C12P 7/6481* (2013.01); *C12P 19/44* (2013.01)

(58) Field of Classification Search
CPC ....... C12P 7/6436; C12P 7/6481; C12P 19/44; C12P 19/445; C12N 1/16; C12N 9/0006; C12N 13/00; C07H 15/10; C11D 1/662
See application file for complete search history.

(56) References Cited

U.S. PATENT DOCUMENTS

| | | |
|---|---|---|
| 2004/0171512 A1 | 9/2004 | Furuta et al. |
| 2016/0324747 A1 | 11/2016 | Ito et al. |
| 2017/0044586 A1 | 2/2017 | Duran |
| 2019/0241917 A1 | 8/2019 | Winterburn et al. |

FOREIGN PATENT DOCUMENTS

| | | | |
|---|---|---|---|
| CN | 109678914 A | 4/2019 | |
| JP | 2003009896 A | 1/2003 | |
| WO | WO-2012167813 A1 * | 12/2012 | ............. C07C 59/01 |

OTHER PUBLICATIONS

Dolman, B. M., et al. "Integrated sophorolipid production and gravity separation." Process Biochemistry 54 (2017): 162-171.
Dolman, B. M., et al. Winterburn. "Integrated production and separation of biosurfactants." Process Biochemistry 83 (2019): 1-8.
Hu, Y., et al. "Purification of lactonic sophorolipids by crystallization." Journal of biotechnology 87.3 (2001): 263-272.
Roelants, S. L. K. W., et al. "Towards the industrialization of new biosurfactants: biotechnological opportunities for the lactone esterase gene from Starmerella bombicola." Biotechnology and bioengineering 113.3 (2016): 550-559.
Saerens, K. M. J., et al. "One-step production of unacetylated sophorolipids by an acetyltransferase negative Candida bombicola." Biotechnology and Bioengineering 108.12 (2011): 2923-2931.
Van Bogaert, I. N. A., et al. "Microbial production and application of sophorolipids." Applied microbiology and biotechnology 76 (2007): 23-34.

\* cited by examiner

*Primary Examiner* — Adam Weidner
*Assistant Examiner* — Tiffany M Gough
(74) *Attorney, Agent, or Firm* — SALIWANCHIK, LLOYD & EISENSCHENK

(57) ABSTRACT

The subject invention provides materials and methods for producing and purifying sophorolipids (SLP). More specifically, the subject invention provides materials and methods for the purification of both hydrophobic and hydrophilic SLP molecules to a purity of, for example, at least 80% by weight, preferably at least 95% by weight, without using solvents or centrifugation. Advantageously, the subject invention is suitable for industrial scale production of purified SLP for use in, for example, cleaning products and detergents, and uses safe and environmentally-friendly materials and processes.

12 Claims, No Drawings

METHODS FOR PURIFICATION OF SOPHOROLIPIDS

CROSS-REFERENCE TO RELATED APPLICATION

This application is a National Stage Application of International Application No. PCT/US2020/065855, filed Dec. 18, 2020; which claims priority to U.S. Provisional Patent Application No. 62/951,058, filed Dec. 20, 2019; and U.S. Provisional Patent Application No. 62/993,158, filed Mar. 23, 2020, each of which is incorporated by reference herein in their entirety.

BACKGROUND OF THE INVENTION

Biosurfactants are a structurally diverse group of surface-active substances produced by microorganisms. All biosurfactants are amphiphiles. They consist of two parts: a polar (hydrophilic) moiety and non-polar (hydrophobic) group. Due to their amphiphilic structure, biosurfactants can, for example, increase the surface area of hydrophobic water-insoluble substances, increase the water bioavailability of such substances, and change the properties of bacterial cell surfaces.

Biosurfactants can also reduce the interfacial tension between water and oil and, therefore, lower the hydrostatic pressure required to move entrapped liquid to overcome the capillary effect. Biosurfactants accumulate at interfaces, thus reducing interfacial tension and leading to the formation of aggregated micellar structures in solution. The formation of micelles provides a physical mechanism to mobilize, for example, oil in a moving aqueous phase. The ability of biosurfactants to form pores and destabilize biological membranes also permits their use as antibacterial, antifungal, and hemolytic agents to, for example, control pest and/or microbial growth.

Like chemical surfactants, the properties of biosurfactants can be measured by hydrophile-lipophile balance (HLB). HLB is the balance of the size and strength of the hydrophilic and lipophilic moieties of a surface-active molecule. Specific HLB values are required for a stable emulsion to be formed. In water/oil and oil/water emulsions, the polar moiety of the surface-active molecule orients towards the water, and the non-polar group orients towards the oil, thus lowering the interfacial tension between the oil and water phases.

HLB values range from 0 to about 20, with lower HLB (e.g., 10 or less) being more oil-soluble and suitable for water-in-oil emulsions, and higher HLB (e.g., 10 or more) being more water-soluble and suitable for oil-in-water emulsions.

There are multiple types of biosurfactants, including low molecular weight glycolipids, lipopeptides, flavolipids and phospholipids, and high molecular weight polymers such as lipoproteins, lipopolysaccharide-protein complexes, and polysaccharide-protein-fatty acid complexes.

Glycolipids, in particular, are biosurfactants comprising a carbohydrate and at least one fatty acid. Glycolipids include, for example, rhamnolipids (RLP), rhamnose-d-phospholipids, trehalose lipids, trehalose dimycolates, trehalose monomycolates, mannosylerythritol lipids (MEL), cellobiose lipids, ustilagic acids and/or sophorolipids (SLP).

Sophorolipids are glycolipids that comprise a sophorose consisting of two glucose molecules, linked to a fatty acid by a glycosidic ether bond. They are categorized into two general forms: the lactonic form, where the carboxyl group in the fatty acid side chain and the sophorose moiety form a cyclic ester bond; and the acidic form, or linear form, where the ester bond is hydrolyzed. In addition to these forms, there exists a number of derivatives characterized by the presence or absence of double bonds in the fatty acid side chain, the length of the carbon chain, the position of the glycosidic ether bond, the presence or absence of acetyl groups introduced to the hydroxyl groups of the sugar moiety, and other structural parameters.

Lactonic and acidic sophorolipids have different functional properties. For example, acidic SLP have higher HLB than lactonic SLP, while lactonic SLP have lower HLB and greater surface tension reducing properties than acidic SLP. Additionally, acidic SLP are highly water soluble due to their free carboxylic acid groups. Combining lactonic and acidic SLP in different ratios affects, e.g., emulsion droplet size, viscosity reducing properties, and surface/interfacial tension reduction properties.

Fermentation of yeast cells in a culture substrate including a sugar and/or lipids and fatty acids with carbon chains of differing length can be used to produce a variety of sophorolipids. The yeast *Starmerella bombicola* is one of the most widely recognized producers of SLP. Typically, the yeast produces both lactonic and acidic SLP during fermentation, with about 60-70% of the SLP comprising lactonic forms, and the remainder comprising acidic forms. Thus, the standard SLP product produced using current production methods can only be used in narrow applications because the range of, e.g., HLB value, is also narrow, e.g., between 4 and 9.

Additionally, because of the nature of biological processes, it is difficult to standardize the exact concentration of pure SLP that can be extracted from a yeast culture medium. Furthermore, crude form SLP can have a cloudy appearance and certain undesirable smell. Thus, in order to ensure a desired concentration and desired appearance and/or smell for a marketable SLP product, it is often necessary to purify the SLP.

Currently, however, obtaining highly purified forms of SLP (e.g., greater than 95%) from a cultivation batch, particularly the acidic form, is challenging and costly. Many methods involve extraction of the SLP by adding organic solvents, such as hexane and/or ethyl acetate, to the liquid SLP product harvested from the culture medium. Other methods include lyophilizing the liquid culture medium, and mixing ethyl acetate with the resulting dried product for about two days at 30° C. The ethyl acetate is then distilled off, and hexane is added to form a crystallized SLP product.

SLP can be used in, for example, food preservation, biomedicine, cosmetics, bioremediation, remediation of heavy metals, and making various household cleaning products. SLP can also be applicable to the petroleum industry in, for example, drilling, cement slurries, fracturing, enhanced oil recovery, scale formation prevention, acidization, demulsification of crude fluids, corrosion inhibition, reduced oil viscosity, cleaning of equipment, waterflooding, and/or foam and steam flooding. Furthermore, in agriculture and livestock production, SLP can be used as, for example, soil amendments, broad spectrum biopesticides, antiviral, antifungal and antibacterial agents, and/or additives to animal feed to enhance nutrient absorption.

While current methods of producing and purifying SLP products can be sufficient for small scale production of SLP, for example, in research settings, these methods are not ideal for industrial applications. The use of flammable organic solvents requires energy and special equipment to treat waste liquid and comply with environmental waste disposal regulations. Additionally, some of the organic solvent may remain in the end product, making it unusable in, for example, food or cosmetics without additional processing.

Therefore, safe, cost-effective and environmentally-friendly methods are needed for purification of sophorolipids that are suitable for industrial scale applications.

BRIEF SUMMARY OF THE INVENTION

The subject invention provides materials and methods for producing and purifying sophorolipids (SLP). More specifically, the subject invention provides materials and methods for the separation of hydrophilic (water-soluble) and hydrophobic (water-insoluble) SLP molecules, as well as purification of SLP to a purity of, for example, at least 80% by weight, preferably at least 95% by weight, without using solvents. Advantageously, the subject invention is suitable for industrial scale production of purified SLP, and uses safe and environmentally-friendly materials and processes.

In preferred embodiments, the methods of the subject invention comprise cultivating a sophorolipid-producing yeast in a submerged fermentation reactor to produce a yeast culture, said yeast culture comprising liquid fermentation broth, yeast cells and a mixture of hydrophobic and hydrophilic SLP; separating the hydrophobic and hydrophilic SLP from one another; and purifying the hydrophobic and hydrophilic SLP.

In preferred embodiments, the sophorolipid-producing yeast is *Starmerella bombicola*, or another member of the *Starmerella* and/or *Candida* clades. For example, *S. bombicola* strain ATCC 22214 can be used according to the subject methods.

According to the subject methods, the hydrophilic and hydrophobic SLP of the SLP mixture are separated after the submerged fermentation cycle is complete. In this step, the entire yeast culture is left to sit with no disturbance for 10 to 50 hours, either in the fermentation reactor, or after being collected into a separate, first collection container. A layer of hydrophobic SLP, the majority of which comprises lactonic SLP (LSL) with trace amounts of hydrophobic acidic SLP (ASL) (e.g., di-acetylated and/or mono-acetylated ASL), will settle at the bottom of the sitting culture.

The settled hydrophobic SLP layer is collected into a second collection container, and a supernatant, which comprises dissolved hydrophilic SLP (e.g., non-acetylated ASL) as well as cells, broth components, and dissolved glucose, is leftover.

In certain embodiments, the hydrophobic SLP layer further comprises impurities, such as yeast cells, glucose, fatty acids and/or other residual materials from fermentation. Thus, in preferred embodiments, the method further comprises purifying the hydrophobic SLP using a "water-washing" method.

In this step, the water-washing method comprises, generally:
a) mixing the hydrophobic SLP with deionized water continuously for about 30 to 300 minutes at a temperature of about 50 to 80° C.;
b) allowing the hydrophobic-water mixture to rest for about 8 to 24 hours, wherein the mixture stratifies into a bottom layer comprising hydrophobic SLP and water, a middle layer comprising water and impurities, and a top foamy layer comprising additional impurities; and
c) collecting the bottom layer into a third collection container and adjusting the water percentage of the bottom layer to produce a water-washed SLP composition.

In preferred embodiments, the final water percentage of the water-washed SLP composition is about 20% to 30% by volume. Thus, in some embodiments, purified water can be added to the water-washed SLP composition or water and mixed continuously for about 1 to 150 minutes at 60 to 80° C. In other embodiments, water can be removed via, for example, spray drying or cyclone evaporation. In certain embodiments, a water percentage at or below 10 to 15% results in crystallization of the SLP, and is therefore undesirable.

Advantageously, the mixing of DI water with the hydrophobic SLP sequesters and accumulates impurities without requiring harmful solvents. In certain embodiments, the ratio of SLP to DI water is about 10:1, 9:1, 8:1, 7:1, 6:1, 5:1, 4:1, or 3:1 by volume.

In some embodiments, the water-washed SLP composition, while free or mostly free of impurities, still comprises a percentage of fatty acid and/or oil impurities due to their hydrophobic nature. For example, in certain embodiments, the water-washed SLP composition may comprise about 10% to 30% by volume of a fatty acid, such as oleic acid.

Thus, in certain embodiments, the method can further comprise removing the fatty acid and/or oil impurities from the water-washed SLP composition to produce hydrophobic SLP with greater purity.

In preferred embodiments, removal of the fatty acids and/or oil impurities comprises applying an oil, preferably a vegetable oil, to the water-washed hydrophobic SLP composition. The mixture of the oil and the water-washed SLP product is mixed at an elevated temperature for at least 60 minutes, after which it is allowed to sit undisturbed for 8 to 24 hours. The undisturbed mixture stratifies into an oil layer and a hydrophobic SLP-water layer. The oil layer can be removed, leaving the hydrophobic SLP layer-water layer with at least 50%, 80%, 98% or more of the fatty acid and oil impurities removed therefrom.

The final product mainly comprises LSL, and some di-acetylated and/or mono-acetylated ASL. In certain embodiments, the HLB of the final product ranges from about 1-8. In certain embodiments, the pH of the final product is about 2.5 to 3.0.

In addition to purification of hydrophobic SLP, in some embodiments, the method comprises purifying hydrophilic (water-soluble) SLP present in the SLP mixture of the yeast culture. Preferably, this is achieved after the hydrophobic SLP in the SLP mixture have been allowed to settle in the fermentation reactor or first collection container. The supernatant that is leftover after the settled hydrophobic SLP is separated from the culture comprises the hydrophilic SLP dissolved therein, as well as residual cells, broth components, and impurities, such as glucose.

In certain embodiments, purification of the hydrophilic SLP comprises removing the cells, broth components and glucose from the supernatant. In this step, the supernatant is collected and centrifuged to separate cellular matter from the liquid component of the supernatant comprising hydrophilic SLP and impurities dissolved therein. The cellular matter can be discarded and/or it can be re-used or recycled, for example, as a fertilizer or animal feed.

This second supernatant resulting from centrifugation can then be transferred to a fourth collection container, or can be returned to the fermentation reactor. Preferably the second supernatant is transferred to a container having aeration capabilities, which can include the original fermentation reactor.

In certain embodiments, glucose, which is water soluble, is one of the only remaining impurities in the second supernatant. Thus, in preferred embodiments, the methods comprise removing the glucose impurities from the second supernatant. In some embodiments, this is achieved using a "yeast digestion" method. In some embodiments, this is achieved using an "enzymatic digestion" method. In certain embodiments, both methods can be used, concurrently, or sequentially.

In one embodiment, the "yeast digestion" method comprises introducing live yeast cells to the second supernatant, e.g., *S. bombicola* or *Wickerhamomyces anomalus*, to produce a supernatant-culture, and providing aeration to the supernatant-culture. After a certain amount of aeration time, for example, 12 to 48 hours, the yeast will consume the remaining glucose as its only carbon source. In certain embodiments, the yeast also produces a small amount of additional SLP into the supernatant-culture.

To extract the hydrophilic SLP, the supernatant-culture can be centrifuged to remove residual cells and then subjected to evaporation to obtain a hydrophilic SLP composition comprising a desired percentage of water. The hydrophilic SLP composition, in comparison to the initial supernatant, will preferably have little or no glucose, e.g., a glucose content of less than 5%, preferably less than 0.5%.

In one embodiment, the "enzymatic digestion" method comprises introducing one or more enzymes into the initial supernatant in order to facilitate or catalyze the digestion of glucose. In certain embodiments, the enzyme is glucose oxidase (GOx).

In certain embodiments, the methods of the subject invention can be carried out in such a way that minimal-to-zero waste products are produced, thereby reducing the amount of fermentation waste being drained into sewage and wastewater systems, and/or being disposed of in landfills. Furthermore, this can be achieved while increasing the overall production of purified SLP from a single fermentation cycle.

Advantageously, the methods can facilitate purification of both hydrophilic and hydrophobic SLP molecules to very high purity, for example, 95%, 98% or greater. Additionally, the methods and equipment of the subject invention reduce the capital and labor costs, as well as the environmental impacts and health hazards, of producing microorganisms and purifying their metabolites on a large scale.

DETAILED DESCRIPTION OF THE INVENTION

The subject invention provides materials and methods for producing and purifying sophorolipids (SLP). More specifically, the subject invention provides materials and methods for the separation and purification of hydrophilic and hydrophobic SLP to a purity of, for example, at least 80% by weight, preferably at least 95% by weight, without using solvents. Advantageously, the subject invention is suitable for industrial scale production of purified SLP, and uses safe and environmentally-friendly materials and processes.
Selected Definitions As used herein, the term "sophorolipid," "sophorolipid molecule," "SLP" or "SLP molecule" includes all forms, and isomers thereof, of SLP molecules, including, for example, acidic (linear) SLP (ASL) and lactonic SLP (LSL). Further included are mono-acetylated SLP, di-acetylated SLP, esterified SLP, SLP with varying hydrophobic chain lengths, SLP with fatty acid-amino acid complexes attached, and other, including those that are and/or are not described within in this disclosure.

In preferred embodiments, the SLP molecules according to the subject invention are represented by General Formula (1) and/or General Formula (2), and are obtained as a collection of 30 or more types of structural homologues having different fatty acid chain lengths ($R^3$), and, in some instances, having an acetylation or protonation at $R^1$ and/or $R^2$.

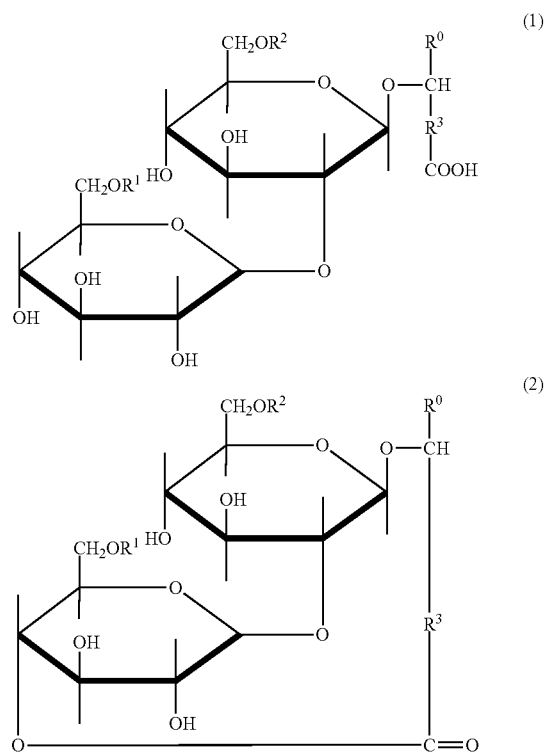

In General Formula (1) or (2), $R^0$ can be either a hydrogen atom or a methyl group. $R^1$ and $R^2$ are each independently a hydrogen atom or an acetyl group. $R^3$ is a saturated aliphatic hydrocarbon chain, or an unsaturated aliphatic hydrocarbon chain having at least one double bond, and may have one or more Substituents.

Examples of the Substituents include halogen atoms, hydroxyl, lower (C1-6) alkyl groups, halo lower (C1-6) alkyl groups, hydroxy lower (C1-6) alkyl groups, halo lower (C1-6) alkoxy groups, and the like. $R^3$ typically has 11 to 20 carbon atoms, preferably 13 to 17 carbon atoms, and more preferably 14 to 16 carbon atoms. Examples of the halogen atoms or halogen atoms bound to alkyl groups or alkoxy groups include fluorine, chlorine, bromine, and iodine.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. The microbes may be present in or removed from the composition. The microbes can be present, with broth in which they were grown, in the microbe-based composition. The cells may be present at, for example, a concentration of at least $1\times10^4$, $1\times10^5$, $1\times10^6$, $1\times10^7$, $1\times10^8$, $1\times10^9$, $1\times10^{10}$, $1\times10^{11}$, $1\times10^{12}$, or more CFU per milliliter of the composition.

The subject invention further provides "microbe-based products," which are products that are to be applied in practice to achieve a desired result. The microbe-based product can be simply a microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, a "biofilm" is a complex aggregate of microorganisms, such as bacteria, wherein the cells adhere to each other and/or to a surface using an extracellular polysaccharide matrix. The cells in biofilms are physiologically distinct from planktonic cells of the same organism, which are single cells that can float or swim in liquid medium.

As used herein, "harvested" refers to removing some or all of a microbe-based composition from a growth vessel.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. An isolated microbial strain means that the strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight the compound of interest. Preferably, the preparation is at least 75%, more preferably at least 90%, and most preferably at least 98%, by weight the compound of interest. For example, a purified compound is one that is preferably at least 80%, 85%, 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism or a substance necessary for taking part in a particular metabolic process. A metabolite can be an organic compound that is a starting material, an intermediate in, or an end product of metabolism. Examples of metabolites include, but are not limited to, enzymes, acids, solvents, alcohols, proteins, vitamins, minerals, microelements, amino acids, biopolymers and biosurfactants.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19 and 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein a "reduction" means a negative alteration, and an "increase" means a positive alteration, wherein the alteration is plus or minus 0.001%, 0.01%, 0.1%, 0.5%, 1%, 5%, 10%, 15%, 20%, 25%, 30%, 35%, 40%, 45%, 50%, 55%, 60%, 65%, 70%, 75%, 80%, 85%, 90%, 95% or 100%.

As used herein, "surfactant" means a compound that lowers the surface tension (or interfacial tension) between two liquids, between a liquid and a gas, or between a liquid and a solid. Surfactants act as, e.g., detergents, wetting agents, emulsifiers, foaming agents, and/or dispersants. A "biosurfactant" is a surface-active substance produced by a living cell.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially of" the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Methods

The subject invention provides materials and methods for producing and purifying sophorolipids (SLP). More specifically, the subject invention provides materials and methods for the separation and purification of hydrophobic and hydrophilic SLP to a purity of, for example, at least 80% by weight, preferably at least 95% by weight, without using solvents. Advantageously, the subject invention is suitable for industrial scale production of purified SLP, and uses safe and environmentally-friendly materials and processes.

In preferred embodiments, the methods of the subject invention comprise cultivating a sophorolipid-producing yeast in a submerged fermentation reactor to produce a yeast culture, said yeast culture comprising liquid fermentation broth, yeast cells and a mixture of hydrophobic and hydrophilic SLP; separating the hydrophobic and hydrophilic SLP from one another; and purifying the hydrophobic and hydrophilic SLP.

Sophorolipids are glycolipid biosurfactants produced by, for example, various yeasts of the *Starmerella* clade. SLP consist of a disaccharide sophorose linked to long chain hydroxy fatty acids. They can comprise a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid is generally 16 or 18 carbon atoms, and may contain one or more unsaturated bonds. Furthermore, the sophorose residue can be acetylated on the 6- and/or 6'-position(s). The fatty acid carboxyl group can be free (acidic or linear form) or internally esterified at the 4"-position (lactonic form). *S. bombicola* produces a specific enzyme, called *S. bombicola* lactone esterase, which catalyzes the esterification of linear SLP to produce lactonic SLP.

In most cases, fermentation of SLP results in a mixture of hydrophobic (water-insoluble) SLP, including, e.g., LSL, mono-acetylated ASL and di-acetylated ASL, and hydrophilic (water-soluble) SLP, including, e.g., non-acetylated ASL.

Due to the structure and composition of SLP, these biosurfactants have excellent surface and interfacial tension reduction properties, as well as other beneficial biochemical properties, which can be useful as a replacement for chemical surfactants in applications such as large scale industrial and agriculture uses, cosmetics, household products, health, medical and pharmaceutical fields, and oil and gas recovery.

In preferred embodiments, the subject invention provides methods of producing sophorolipidic compositions by cultivating a sophorolipid-producing yeast using submerged fermentation. The methods can be scaled up or down in size. Most notably, the methods can be scaled to an industrial scale, i.e., a scale that is suitable for use in supplying biosurfactants in amounts to meet the demand for commercial applications, for example, production of compositions for agriculture and enhanced oil recovery.

The microorganisms utilized according to the subject invention may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganism is any yeast or fungus. Examples of yeast and fungus species suitable for use according to the current invention, include, but are not limited to, *Acaulospora, Aspergillus, Aureobasidium* (e.g., *A. pullulans*), *Blakeslea, Candida* (e.g., *C. albicans, C. apicola*), *Cryptococcus, Debaryomyces* (e.g., *D. hansenii*), *Entomophthora, Fusarium, Hanseniaspora* (e.g., *H. uvarum*), *Hansenula, Issatchenkia, Kluyveromyces, Mortierella, Mucor* (e.g., *M. piriformis*), *Meyerozyma* (e.g., *M Penicillium, Phythium, Phycomyces, Pichia* (e.g., *P. anomala, P. guilliermondii, P. occidentalis, P. kudriavzevii*), *Pseudozyma* (e.g., *P. aphidis*), *Rhizopus, Saccharomyces* (*S. cerevisiae, S. boulardii sequela, S. torula*), *Starmerella* (e.g., *S. bombicola*), *Torulopsis, Thraustochytrium, Trichoderma* (e.g., *T. reesei, T. harzianum, T. virens*), *Ustilago* (e.g., *U. maydis*), *Wickerhamomyces* (e.g., *W. anomalus*), *Williopsis*, and *Zygosaccharomyces* (e.g., *Z. bailii*).

In preferred embodiments, microorganism is a *Starmerella* spp. yeast and/or *Candida* spp. yeast, e.g., *Starmerella (Candida) bombicola, Candida apicola, Candida batistae, Candida floricola, Candida riodocensis, Candida stellate* and/or *Candida kuoi*. In a specific embodiment, the microorganism is *Starmerella bombicola*, e.g., strain ATCC 22214.

In one embodiment, the method comprises filling a fermentation reactor with a liquid nutrient medium; inoculating the reactor with a sophorolipid-producing yeast to produce a yeast culture; and cultivating the yeast culture under conditions favorable for production of SLP.

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, samples may be taken from the vessel for enumeration, purity measurements, SLP concentration, and/or visible oil level monitoring. For example, in one embodiment, sampling can occur every 24 hours.

The microbial inoculant according to the subject methods preferably comprises cells and/or propagules of the desired microorganism, which can be prepared using any known fermentation method. The inoculant can be pre-mixed with water and/or a liquid growth medium, if desired.

In certain embodiments, the cultivation method utilizes submerged fermentation in a liquid growth medium. In one embodiment, the liquid growth medium comprises a carbon source. The carbon source can be a carbohydrate, such as glucose, dextrose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as canola oil, soybean oil, rice bran oil, olive oil, corn oil, sunflower oil, sesame oil, and/or linseed oil; powdered molasses, etc. These carbon sources may be used independently or in a combination of two or more. In preferred embodiments, a hydrophilic carbon source, e.g., glucose, and a hydrophobic carbon source, e.g., oil or fatty acids, are used.

In some embodiments, the cultivation method utilizes reduced amounts of a carbon source, compared with standard methods in the art. For example, in some embodiments, the liquid growth medium can comprise a sugar (e.g., glucose) and an oil (e.g., canola oil) at amounts of 25-70 g/L and 25-70 ml/L, respectively. Advantageously, in some embodiments, reducing the amount of sugar and oil in the liquid growth medium reduces the amount of glucose and/or oil impurities left in the culture, thus enhancing the ability to purify the SLP molecules to greater degrees of purity.

In one embodiment, the liquid growth medium comprises a nitrogen source. The nitrogen source can be, for example, yeast extract, potassium nitrate, ammonium nitrate, ammonium sulfate, ammonium phosphate, ammonia, urea, and/or ammonium chloride. These nitrogen sources may be used independently or in a combination of two or more.

In one embodiment, one or more inorganic salts may also be included in the liquid growth medium. Inorganic salts can include, for example, potassium dihydrogen phosphate, monopotassium phosphate, dipotassium hydrogen phosphate, disodium hydrogen phosphate, potassium chloride, magnesium sulfate, magnesium chloride, iron sulfate, iron chloride, manganese sulfate, manganese chloride, zinc sulfate, lead chloride, copper sulfate, calcium chloride, calcium carbonate, calcium nitrate, magnesium sulfate, sodium phosphate, sodium chloride, and/or sodium carbonate. These inorganic salts may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, proteins and microelements can be included, for example, corn flour, peptone, yeast extract, potato extract, beef extract, soybean extract, banana peel extract, and the like, or in purified forms. Amino acids such as, for example, those useful for biosynthesis of proteins, can also be included.

The method of cultivation can further provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid. In certain embodiments, dissolved oxygen (DO) levels are maintained at about 25% to about 75%, about 30% to about 70%, about 35% to about 65%, about 40% to about 60%, or about 50% of air saturation.

In some embodiments, the method for cultivation may further comprise adding additional acids and/or antimicrobials in the liquid medium before and/or during the cultivation process. Antimicrobial agents or antibiotics (e.g., streptomycin, oxytetracycline) are used for protecting the culture against contamination. In some embodiments, however, the metabolites produced by the yeast culture provide sufficient antimicrobial effects to prevent contamination of the culture.

In one embodiment, prior to inoculation, the components of the liquid culture medium can optionally be sterilized. In one embodiment, sterilization of the liquid growth medium can be achieved by placing the components of the liquid culture medium in water at a temperature of about 85-100° C. In one embodiment, sterilization can be achieved by dissolving the components in 1 to 3% hydrogen peroxide in a ratio of 1:3 (w/v).

In one embodiment, the equipment used for cultivation is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Gaskets, openings, tubing and other equipment parts can be sprayed with, for example, isopropyl alcohol.

Air can be sterilized by methods know in the art. For example, the ambient air can pass through at least one filter before being introduced into the vessel. In other embodiments, the medium may be pasteurized or, optionally, no heat at all added, where the use of pH and/or low water activity may be exploited to control unwanted microbial growth.

The pH of the culture should be suitable for the microorganism of interest. In some embodiments, the pH is about 2.0 to about 7.0, about 3.0 to about 5.5, about 3.25 to about 4.0, or about 3.5. Buffers, and pH regulators, such as carbonates and phosphates, may be used to stabilize pH near a preferred value. In certain embodiments, a base solution is used to adjust the pH of the culture to a favorable level, for example, a 15% to 30%, or a 20% to 25% NaOH solution. The base solution can be included in the growth medium and/or it can be fed into the fermentation reactor during cultivation to adjust the pH as needed.

In one embodiment, the method of cultivation is carried out at about 5° to about 100° C., about 15° to about 60° C., about 20° to about 45° C., about 22° to about 35° C., or about 24° to about 28° C. In one embodiment, the cultivation may be carried out continuously at a constant temperature. In another embodiment, the cultivation may be subject to changing temperatures.

According to the subject methods, the microorganisms can be incubated in the fermentation system for a time period sufficient to achieve a desired effect, e.g., production of a desired amount of cell biomass or a desired amount of one or more microbial growth by-products. The microbial growth by-product(s) produced by microorganisms may be retained in the microorganisms and/or secreted into the growth medium. The biomass content may be, for example from 5 g/l to 180 g/l or more, from 10 g/l to 150 g/l, or from 20 g/l to 100 g/l.

In certain embodiments, fermentation of the yeast culture occurs for about 100 to 150 hours, or about 115 to about 125 hours, or about 120 hours. In some embodiments, the fermentation cycle is ended once the glucose and/or oil concentrations in the medium are exhausted (e.g., at a level of 0% to 0.5%). In some embodiments, the end of the fermentation cycle is determined to be a time point when the microorganisms have begun to consume trace amounts of SLP.

According to the subject methods, the hydrophilic and hydrophobic SLP of the SLP mixture are separated after the submerged fermentation cycle is complete. In this step, the entire yeast culture is left to sit undisturbed for 10 to 50 hours, either in the fermentation reactor, or after being collected into a separate, first collection container. In preferred embodiments, an "undisturbed" culture is one that is not altered or interfered with physically or chemically. For example, an undisturbed culture is one that is resting, rather than being subjected to moving, mixing, or addition or removal of components.

A layer of hydrophobic SLP, the majority of which comprises LSL with trace amounts of hydrophobic di-acetylated and/or mono-acetylated ASL (e.g., approximately 10:1 to 4:1, LSL to ASL), will settle at the bottom of the sitting culture. The settled hydrophobic SLP layer is collected into a second collection container, and a supernatant, which comprises dissolved hydrophilic SLP (e.g., non-acetylated ASL) as well as cells, broth components, and dissolved glucose, is leftover. In certain embodiments, the hydrophobic SLP layer comprises about 75% to 85%, or about 80% of the total SLP produced in the yeast culture.

Purification of Hydrophobic SLP

In certain embodiments, the hydrophobic SLP layer further comprises impurities, such as yeast cells, glucose, fatty acids and/or other residual materials from fermentation. Thus, in preferred embodiments, the method further comprises purifying the hydrophobic SLP using a "water-washing" method. In preferred embodiments, the water-washing method comprises, generally:
  a) mixing the hydrophobic SLP with deionized (DI) water continuously for about 30 to 300 minutes at a temperature of about 50 to 80° C.;
  b) allowing the hydrophobic-water mixture to rest for about 8 to 24 hours, wherein the mixture stratifies into a bottom layer comprising hydrophobic SLP and water, a middle layer comprising water and impurities, and a top foamy layer comprising additional impurities; and
  c) collecting the bottom layer into a third collection container and adjusting the water percentage of the bottom layer to produce a water-washed SLP composition.

In certain embodiments, the hydrophobic SLP-water mixture of a) is continuously mixed/agitated in the second collection container for about 30 to 300 minutes, or about 60 to 180 minutes, at a temperature of about 50° C. to 80° C., about 55° C. to 75° C., or about 60° C. to 70° C.

Advantageously, the mixing of DI water with the hydrophobic SLP sequesters and accumulates impurities without requiring harmful solvents. In certain embodiments, the ratio of SLP to DI water is about 10:1 to 1:10 (volume of SLP to volume of water), or about 5:1, or 4:1 to 3:1 by volume.

In certain embodiments, the hydrophobic SLP-water mixture of a) is left to rest for an amount of time in b) until the temperature reduces to about 25° C. to 45° C., or about 30° C. to 35° C.

In some embodiments, the bottom layer of c), while free, or mostly free, of impurities, still comprises a percentage of water. In certain embodiments, the percentage of water is about 15% to 75%, or about 25% to 50% by volume.

In preferred embodiments, the final water percentage of the water-washed SLP composition is about 20% to 30% by volume. Thus, in some embodiments, purified water can added to the water-washed SLP composition or water and mixed continuously for about 100 to 150 minutes at 60 to 80° C. In other embodiments, water can be removed via, for example, spray drying or cyclone evaporation. In certain embodiments, a water percentage at or below 10 to 15% can result in crystallization of the SLP, and therefore is typically undesirable.

In some embodiments, the water-washed SLP composition, while free or mostly free of impurities, still comprises a percentage of fatty acid and/or oil impurities due to their hydrophobic nature. For example, in certain embodiments, the water-washed SLP composition may comprise about 10% to 30% by volume of a fatty acid and/or oil impurity, such as oleic acid.

As used herein, "fatty acid and/or oil impurities" include fatty acids and/or sources thereof that are present in SLP compositions as a result of fermentation of the SLP. Fatty acids are carboxylic acids with a long aliphatic chain that can be saturated or unsaturated. Fatty acids, whether in free form or as a component of an oil, are often used as carbon or other nutrient sources in microbial fermentation.

In certain embodiments, the fatty acid and/or oil impurities in the SLP compositions can contain one or more saturated fatty acids, unsaturated fatty acids, short-fatty acids, medium-chain fatty acids, long-chain fatty acids, very long-chain fatty acids, fatty acids having from 8 to 22 or more carbons, and/or fatty acids having from 1 to 6 double bonds.

In certain embodiments, the fatty acid and/or oil impurities can contain any of the following fatty acids: caprylic acid, capric acid, lauric acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, and arachidonic acid.

In certain embodiments, the fatty acid and/or oil impurities can contain any of the following oils and/or sources of fatty acids: peanut oil, olive oil, palm oil, soybean oil, rapeseed oil, cocoa butter, rice bran oil, sunflower oil, coconut oil, corn oil, cottonseed oil, palm oil, safflower oil, and/or sesame oil.

Thus, in certain embodiments, the method can further comprise removing the fatty acid and/or oil impurities from the water-washed SLP composition to produce hydrophobic SLP with greater purity.

In certain embodiments, an oil is added to the water-washed hydrophobic SLP composition. The added oil can be, for example, a plant (vegetable) oil, such as, for example, canola oil, peanut oil, olive oil, palm oil, soybean oil, rapeseed oil, cocoa butter, rice bran oil, sunflower oil, coconut oil, corn oil, cottonseed oil, palm oil, safflower oil, or sesame oil; or mineral oils such as, for example, food grade mineral oil. The added oil can be added to the water-washed SLP composition at a ratio of at least 1:2 (added oil:SLP), 2:1, 5:1, 10:1, or greater concentrations of added oil relative to SLP. In a preferred embodiment, canola oil is added at a concentration of 10:1 (canola oil:SLP) to the water-washed SLP composition.

In certain embodiments the water-washed SLP and oil mixture is mixed for about 30 to 300 minutes, or about 60 to 180 minutes, at a temperature of about 50° C. to 80° C., about 55° C. to 75° C., or about 60° C. to 70° C.

After the mixing is complete, the mixture is left to sit undisturbed for about 6 hours to about 48 hours, about 8 to about 42 hours, about 12 hours to about 36 hours, or about 16 hours to about 24 hours until the mixture stratifies into two layers: a hydrophobic SLP/water layer and an oil layer. In one embodiment, the oil layer comprises the added oil and the fatty acid and/or oil impurities.

In certain embodiments, an electric current can be applied to the mixture. The current can be applied during the mixing of the water-washed SLP composition and added oil, and/or it can be applied during the stratification of the oil layer and the SLP/water layer. In a preferred embodiment, the electric current can destabilize oil-in-water emulsions to facilitate the coalescence of oil. The electric current can be alternating current (AC), direct current (DC), or a combination of each. The electric current can be present during the entire stratification and mixing processes. Alternatively, the electric current can be pulsed at a single time point or at multiple time points throughout the stratification and/or mixing processes. In a preferred embodiment, pulsed alternating and direct currents are applied to the composition until stratification of the oil and SLP/water layers is achieved.

In certain embodiments, after stratification of the hydrophobic SLP/water layer and oil layer, the oil layer, now containing the fatty acid and/or oil impurities, can be removed from the top of the composition. The purified hydrophobic SLP and water layer can be harvested from the bottom of the container in which the layer resides. In certain embodiments, the oil layer can be collected and reused to remove fatty acids and oil impurities from other SLP compositions and/or as a nutrient source in other microbial fermentation processes.

In some embodiments, removal of fatty acid and/or oil impurities according to the subject invention can be performed on hydrophobic SLP compositions that have not been subjected to water washing. For example, after a SLP fermentation cycle has run and the yeast culture is allowed to sit undisturbed until the hydrophobic SLP layer settles to the bottom of the culture, the settled SLP layer can be collected, optionally, centrifuged to remove cell matter, and either treated directly with an added oil (e.g., canola oil) according to the subject methods, or it can be subjected to other known purification methods, such as ethyl acetate washing, prior to applying the added oil treatment.

In certain embodiments, the subject invention provides compositions produced according to the subject methods, the compositions comprising purified hydrophobic SLP and water. In preferred embodiments, the percentage of fatty acids in the purified SLP composition is less than 10%, 5%, 2.5%, 1%, 0.5%, or even less, whereby at least 50%, 80%, 95%, 98%, or a greater amount of the fatty acids are removed from the lipophilic SLP composition. In certain embodiments, the compositions produced according to the subject methods have lower CMCs compared to SLP compositions that are not purified with added oil to remove fatty acid and oil impurities.

The final product mainly comprises LSL, and some di-acetylated and/or mono-acetylated ASL. In certain embodiments, the HLB of the final product ranges from about 1-8. In certain embodiments, the pH of the final product is about 2.5 to 3.0.

Advantageously, the methods can enable purification of SLP to extremely high purity, for example, 95%, 98% or greater.

In some embodiments, the composition can be stored in a container until use. The storage time is preferably short. Thus, the storage time may be less than 60 days, 45 days, 30 days, 20 days, 15 days, 10 days, 7 days, 5 days, 3 days, 2 days, 1 day, or 12 hours.

Purification of Hydrophilic SLP

In addition to purification of hydrophobic SLP, in preferred embodiments, the method comprises purifying hydrophilic (water-soluble) SLP present in the SLP mixture of the yeast culture produced during fermentation of the sophorolipid-producing yeast. Preferably, this is achieved after the hydrophobic SLP in the SLP mixture have been allowed to settle in the fermentation reactor or first collection container. The supernatant that is leftover after the settled hydrophobic SLP is separated from the yeast culture comprises the hydrophilic SLP dissolved therein, as well as residual cells, broth components, and impurities, such as glucose.

In certain embodiments, purification of the hydrophilic SLP comprises removing the cells, broth components and glucose from the supernatant. In this step, the supernatant is collected and centrifuged to separate cellular matter from the liquid component of the supernatant comprising hydrophilic SLP and impurities dissolved therein. The cellular matter can be discarded and/or it can be re-used or recycled, for example, as a fertilizer or animal feed.

This second supernatant resulting from centrifugation can then be transferred to a fourth collection container, or can be returned to the fermentation reactor. Preferably the second supernatant is transferred to a container having aeration capabilities, which can include the original fermentation reactor.

In certain embodiments, glucose, which is water soluble, is the one, or one of the, only remaining impurities in the second supernatant. Thus, in preferred embodiments, the methods comprise removing the glucose impurities from the second supernatant. In some embodiments, this is achieved using a "yeast digestion" method. In some embodiments, this is achieved using an "enzymatic digestion" method. In certain embodiments, both methods can be used, concurrently, or sequentially.

In one embodiment, the "yeast digestion" method comprises introducing live yeast cells to the second supernatant, e.g., *S. bombicola* or *Wickerhamomyces anomalus*, to produce a supernatant-culture, and providing aeration to the supernatant-culture. After a certain amount of aeration time, for example, 12 to 48 hours, the yeast will consume the remaining glucose as its only carbon source. In certain embodiments, the yeast also produces a small amount of additional SLP into the supernatant-culture.

To extract the hydrophilic SLP, the supernatant-culture can be centrifuged to remove residual cells and then subjected to evaporation to obtain a hydrophilic SLP composition comprising a desired percentage of water. The hydrophilic SLP composition, in comparison to the initial supernatant, will preferably have little or no glucose, e.g., a glucose content of less than 5%, preferably less than 0.5%.

In one embodiment, the "enzymatic digestion" method comprises introducing one or more enzymes into the initial supernatant in order to facilitate or catalyze the digestion of glucose. In certain embodiments, the enzyme is glucose oxidase (GOx).

GOx catalyzes the production of gluconic acid and hydrogen peroxide from glucose. The hydrogen peroxide, depending on the application of the final SLP product, can be either evaporated or left in the product to, for example, increase its antibacterial activity. Gluconic acid is non-toxic, biodegradable, antibacterial and can have positive detergent activity.

Further Processing of SLP Products

In one embodiment, when it is desired to produce even more hydrophilic SLP from one submerged cultivation cycle, the hydrophobic SLP can be converted into water-soluble hydrophilic SLP.

During the water-washing purification method, the bottom hydrophobic SLP layer of the stratified SLP-water mixture can be mixed with a base to adjust the pH to, e.g., about 4 to 7, or about 4.2 to 6.8. In certain embodiments, this is achieved by titrating small amounts (e.g., 0.1 µl to 10 ml per titration) of NaOH or another base into the mixture, wherein the increased pH causes hydrolysis of the LSL ester bond, converting the lactonic molecule to a linear molecule.

In certain embodiments, the functional properties of the SLP product can be analyzed to determine whether it has been converted into a hydrophilic product, for example, by testing its capabilities as an emulsifier or other HLB-specific characteristics.

In certain embodiments, the methods of the subject invention can be carried out in such a way that minimal-to-zero waste products are produced, thereby reducing the amount of fermentation waste being drained into sewage and wastewater systems, and/or being disposed of in landfills. Furthermore, this can be achieved while increasing the overall SLP production from a single fermentation cycle.

The yeast cell biomass collected from the yeast culture after removal and purification of the SLP would typically be inactivated and disposed of. However, the subject methods can further comprise collecting the cell biomass and using it, in live or inactive form, for a variety of purposes, including but not limited to, as a soil amendment, a livestock feed supplement, an oil well treatment, and/or a skincare product. The cell biomass can be used directly, or it can be mixed with additives specific for the intended use.

In certain embodiments, the subject invention provides compositions produced according to the subject methods, the compositions comprising a purified SLP and water. In preferred embodiments, the percentage of water in the composition, by volume, is about 20% to 50%, preferably about 20% to 30%.

The purified SLP of the composition can be, for example, a lactonic, linear, mono-acetylated lactonic or linear, and/or di-acetylated lactonic or linear sophorolipid. In certain embodiments, the composition comprises more than one purified SLP molecule.

In some embodiments, the composition can be stored in a container until use. The storage time is preferably short. Thus, the storage time may be less than 60 days, 45 days, 30 days, 20 days, 15 days, 10 days, 7 days, 5 days, 3 days, 2 days, 1 day, or 12 hours.

Combined with the characteristics of low toxicity and biodegradability, SLP are advantageous for use in many settings including, for example, improved bioremediation, mining, and oil and gas production; waste disposal and treatment; enhanced health of livestock and other animals; food additives, such as preservatives and/or emulsifiers; cosmetic additives; and enhanced health and productivity of plants.

Further components can be added to the sophorolipidic compositions as needed for a particular use. The additives can be, for example, buffers, carriers, other microbe-based compositions produced at the same or different facility, viscosity modifiers, preservatives, nutrients for microbe growth, nutrients for plant growth, solvents, tracking agents, pesticides, herbicides, animal feed, food products and other ingredients specific for an intended use.

Cultivation of microbial biosurfactants according to the prior art is a complex, time and resource consuming, process that requires multiple stages. Advantageously, the methods of the subject invention do not require complicated equipment or high energy consumption, and thus reduce the capital and labor costs of producing microorganisms and their metabolites on a large scale. Additionally, the methods and equipment of the subject invention reduce the capital and labor costs of purifying microbial metabolites on a large scale.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Cultivation of *Starmerella Bombicola* for SLP Production and Purification of SLP Preparation A stainless steel fermentation reactor is used for the production of SLP. The reactor comprises about 150 gallons of water, into which a medium comprising dextrose (25 to 150 g/L), yeast extract (1 to 10 g/L), canola oil (25 ml/L to 110 ml/L) and urea (0.5 to 5 g/L) is added.

The reactor comprises a mixing apparatus for continuous agitation and mixing of the culture. The reactor with medium is steamed at 100° C. for about 60 minutes in order to sterilize the reactor and the growth medium.

The reactor is then allowed to cool down. Once the reactor reaches about 35° C., antibiotics are added to the medium to prevent bacterial contamination. The antibiotic composition comprises 300 g streptomycin and 20 g oxytetracycline dissolved in 4 L DI water. Other reactor tubing and openings are sprayed with isopropyl alcohol (IPA) to sterilize them.

Small-scale reactors are used for growing *Starmerella bombicola* inoculum cultures. The culture is grown for at least 42 to 48 hours at 26 to 28° C. in the small-scale reactors.

Once the stainless-steel fermentation reactor reaches 30° C., it is then inoculated with about 25 L of the inoculum culture.

Fermentation

The temperature of fermentation is held at 23 to 28° C. After about 22 to 26 hours, the pH of the culture is set to about 3.0 to 4.0, or about 3.5, using 20% NaOH. The fermentation reactor comprises a computer that monitors the pH and controls the pump used to administer the base, so that the pH remains at 3.5.

After about 6-7 days of cultivation (120 hours+/−1 hour), if 7.5 ml of a SLP layer is visible, the batch is ready for harvesting. In some instances, there is also minimal oil visible and minimal glucose detected (e.g., about 0% to 0.5%).

Harvesting

The culture is harvested to a first collection container and left undisturbed for 24 to 48 hours. A layer of hydrophobic SLP settles to the bottom of the first collection container.

Example 2—Water Washing for Purification of Lipophilic SLP Molecule

The settled hydrophobic SLP layer, containing approximately 60-70% LSL and 30-40% hydrophobic ASL, is harvested to a second collection container, leaving behind a supernatant. DI water is mixed with the SLP layer at a ratio of 4:1 to 3:1, SLP to water (volume). The mixture is warmed to a temperature of about 60° C. to 70° C. and mixed for 1 to 2 hours.

Mixing is halted and the mixture is allowed to rest for 8 to 24 hours, or until the temperature of the mixture lowers naturally to about 25° C. to 35° C. The mixture forms three layers: a bottom layer comprising hydrophobic SLP and water; a middle layer comprising water and impurities, such as yeast cells, glucose, and fatty acids; and a top layer comprising impurities in foam.

The bottom hydrophobic SLP-water layer is drained from the second container into a third container, and the water content is adjusted so that it is below 50% but above about 10% to 15% by volume. Ideally, the water content is about 20% by volume.

The water content can be reduced via evaporation, using either a cyclone evaporator or a spray dryer at 60° C. The water content can be increased by adding purified water and mixing it with the SLP for about 1 to 2 hours at 70° C.

The purified product, the water-washed SLP composition, has an HLB of about 1 to 8, with the SLP portion comprising about 80 to 90% hydrophobic SLP molecules, such as LSL, and di-acetylated and/or mono-acetylated ASL.

The middle and top layers can be subjected to water washing again to recover additional hydrophobic SLP.

Example 3—Water-Washing Scaling Study

Water-washing procedures were conducted on a laboratory scale, on a pilot scale and on an industrial scale to determine the feasibility of the process for all levels of SLP production and purification. The following results were obtained.

Typical Characteristics of Hydrophobic Product:
CMC from 50 to 100;
Surface Tension Reduction at CMC from 35 to 39;
HLB from 2 to 7;
No phase separation;
No live cells;
Glucose content no higher than 0.1%;
Not soluble in water;
Dispersible in water, creates milky solution;
No foam produced when mixed with water;

Laboratory Scale Purification Analysis
Water content: 23%
Glucose content: 0.04%
Oleic acid content: 20%
SLP content: 57.5%

SLP Species:
Linear oleic acid non-acetylated: 0.9%
Linear oleic acid mono-acetylated: 3.22%
Lactonic oleic acid mono-acetylated: 9.6%
Lactonic linoleic acid mono-acetylated: 1.96%
Lactonic oleic acid di-acetylated: 29.06%
Lactonic stearic acid di-acetylated: 2.97%
Linear oleic acid di-acetylated: 8%
Linear linoleic acid di-acetylated: 0%

Pilot Scale Purification Analysis
Water content: 14%
Glucose content: 0%
Oleic acid content: 15%
SLP content: 72%

SLP Species:
Linear oleic acid non-acetylated: 1.41%
Linear oleic acid mono-acetylated: 5.12%
Lactonic oleic acid mono-acetylated: 8.6%
Lactonic linoleic acid mono-acetylated: 3.11%
Lactonic oleic acid di-acetylated: 25.22%
Lactonic stearic acid di-acetylated: 6.21%
Linear oleic acid di-acetylated: 18.71%
Linear linoleic acid di-acetylated: 3.8%

Industrial Scale Purification Analysis
Water content: 19%
Glucose content: 0.05%
Oleic acid content: 23%
SLP content: 58%

SLP Species:
Linear oleic acid non-acetylated: 0.96%
Linear oleic acid mono-acetylated: 5.04%
Lactonic oleic acid mono-acetylated: 13.52%
Lactonic linoleic acid mono-acetylated: 1.13%
Lactonic oleic acid di-acetylated: 23.28%
Lactonic stearic acid di-acetylated: 2.99%
Linear oleic acid di-acetylated: 10.06%
Linear linoleic acid di-acetylated: 0%

Example 4—Removal of Residual Oleic Acid From Hydrophobic SLP

To obtain a low HLB hydrophobic SLP composition with a low oil impurities content, the water-washed SLP composition is further purified through the addition of canola oil. The oil is added to the water-washed SLP composition at a ratio of 1:2 (added oil:SLP), 2:1, 5:1, or 10:1.

Then, the water-washed SLP composition and oil is mixed for 2 hours, or about 1 to 2.5 hours at a temperature of 60° C. After mixing, the entire composition is left to sit undisturbed overnight (or about 16 hours) to stratify the hydrophobic SLP and water layer from the added oil layer, which now contains oil and fatty acid and/or oil impurities.

After the stratification of the layers, the oil layer can be removed to obtain a hydrophobic SLP product with greater purity.

As illustrated in Tables 1 and 2, the majority of fatty acids in the water-washed SLP compositions can be removed. Furthermore, as illustrated in Table 1, the addition of canola oil at a ratio of 10:1 (canola oil:SLP) removes 98% of the fatty acids from the SLP composition. This is a significant decrease of the fatty acid concentration, leaving a purified SLP composition with a fatty acid concentration of 0.48%, compared to the 23.54% fatty acid concentration of the water-washed SLP composition.

TABLE 1

Fatty acid content in SLP composition after oil purification of SLP (23.53% Fatty acids initially)

| Ratio of canola oil to SLP | Fatty acid concentration after oil purification |
|---|---|
| 1:2 | 9.5% |
| 2:1 | 4.46% |
| 5:1 | 2.51% |
| 10:1 | 0.48% |

TABLE 2

Fatty acid content in SLP composition after oil purification of SLP (19.62% Fatty acids initially)

| Ratio of canola oil to SLP | Fatty acid concentration after oil purification |
|---|---|
| 5:1 | 2.17% |

TABLE 3

CMC of SLP composition

| Sample | CMC |
|---|---|
| Water washed SLP | 113 |
| Water washed SLP treated with canola oil | 57 |

Table 3 illustrates that the composition purified with the canola oil has a lower CMC compared to the water-washed SLP composition.

Example 5—Purification of Hydrophilic SLP

To obtain hydrophilic SLP from the yeast culture produced according to Example 1, supra, the supernatant, comprising dissolved hydrophilic SLP, cells, and broth components, such as glucose, can be centrifuged to remove cellular matter and then the supernatant is subjected to yeast digestion and/or enzymatic digestion to remove glucose impurities.

Yeast Digestion

The supernatant is placed into a container with aeration capabilities. Additional live yeast cells, such as *S. bombicola*, are introduced into the supernatant, which is then aerated for 12 to 48 hours. The *S. bombicola* consume residual glucose within the supernatant and will produce small amounts of SLP. Then, the supernatant-culture is centrifuged to produce a pellet comprising residual cells and a second supernatant that comprises the glucose-free hydrophilic SLP in liquid.

The second supernatant is evaporated to adjust the water content to, preferably, 20% to 30%. The resulting product will have an HLB of 10 or above, and in comparison to the initial supernatant, will have zero, or insignificant amounts of, glucose.

Enzymatic Digestion of Glucose Impurities

Glucose oxidase (GOx) enzyme is added to the supernatant after centrifugation. GOx catalyzes the conversion of glucose to gluconic acid and hydrogen peroxide. Hydrogen peroxide can be either evaporated or left in the product to, for example, increase its antibacterial activity. Digestion of glucose in this manner results in higher purity hydrophilic SLP.

Example 6—Surfactant HLB Values Based on Intended Use—Cleaning Products

The purified SLP compositions obtained using methods according to embodiments of the subject invention can be used for household and industrial cleaning products. As shown in Table 4 below, the use is determined based on, for example, the hydrophobic or hydrophilic nature of the purified composition, which is a factor determining the HLB value of the composition.

TABLE 4

SLP HLB value based on desired application for HI&I cleaning products.

| HLB Value | Uses | |
|---|---|---|
| 1-3 | Antifoaming agent in detergents where foam is unfavorable | More hydrophobic |
| 3-6 | Antimicrobial/antifungal soaps (without need for antibiotic or antifungal drugs) Sanitizers for surface disinfection W/O emulsification | |
| 7-9 | Cleaning of porous surfaces (HLB up to 9) Pine oil and d-limonene cleaners Vehicle cleaners Spray-dried detergents | |
| 10-14 | Active ingredient in detergent (as opposed to an adjuvant) Degreasing booster Vehicle cleaners Laundry detergent Dish soap/detergent | More hydrophilic |
| 13-18 | Active ingredient in detergent (as opposed to an adjuvant) O/W emulsification | |
| 19-22 | Foaming agent in detergents | |

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

We claim:

1. A method for producing a purified sophorolipid (SLP) composition, the method comprising:
    cultivating a sophorolipid-producing yeast in a submerged fermentation reactor to produce a yeast culture, said yeast culture comprising liquid fermentation medium, yeast cells and a mixture of hydrophobic SLP and hydrophilic SLP;
    separating the hydrophobic and hydrophilic SLP by allowing the yeast culture to sit undisturbed at the end of the cultivation cycle in the fermentation reactor or in a first collection container for 12 to 50 hours, wherein a layer comprising hydrophobic SLP settles to the bottom of the yeast culture, and collecting the settled hydrophobic SLP layer into a second collection container, leaving behind a supernatant comprising dissolved hydrophilic SLP; and
    purifying the hydrophobic SLP and/or the hydrophilic SLP;
    wherein the hydrophobic SLP layer further comprises impurities, selected from yeast cells, glucose, fatty acids and other residual materials from fermentation, wherein purifying the hydrophobic SLP comprises water-washing the hydrophobic SLP layer according to the following steps:
        a) mixing the hydrophobic SLP layer with deionized water continuously for about 30 to 300 minutes at a temperature of about 50 to 80° C.;
        b) allowing the hydrophobic-water mixture to rest for about 8 to 24 hours, wherein the mixture stratifies into a bottom layer comprising hydrophobic SLP and water, a middle layer comprising water and impurities, and a top foamy layer comprising additional impurities; and
        c) collecting the bottom layer into a third collection container to produce a water-washed SLP composition; and
    wherein the purified hydrophobic SLP composition comprises lactonic SLP, di-acetylated linear SLP and/or mono-acetylated linear SLP.

2. The method of claim 1, wherein the yeast is *Starmerella bombicola*.

3. The method of claim 1, wherein the middle layer of the stratified mixture of the hydrophobic SLP-containing layer and water comprises water and impurities, said impurities comprising residual yeast cells, glucose and/or fatty acids.

4. The method of claim 1, wherein the top layer of the stratified mixture of the hydrophobic SLP-containing layer and water comprises foam and impurities, said impurities comprising residual yeast cells, glucose and/or triglycerides from fermentation.

5. The method of claim 1, wherein the percentage of water in the collected bottom layer is adjusted so that it is less than 50%.

6. The method of claim 1, wherein the water-washed SLP composition comprises one or more fatty acid and/or oil impurities, and wherein the method further comprises removing the fatty acid and/or oil impurities.

7. The method of claim 6, wherein the fatty acid and/or oil impurity is oleic acid.

8. The method of claim 1, wherein the purified SLP composition has a hydrophile-lipophile balance (HLB) value of about 1 to 8.

9. The method of claim 1, wherein the supernatant comprises hydrophilic SLP and glucose impurities dissolved therein, and wherein the method further comprises centrifuging the supernatant to remove cellular material and removing glucose impurities in the supernatant using a yeast digestion method and/or an enzymatic digestion method.

10. A method for producing a purified sophorolipid (SLP) composition, the method comprising:
    cultivating a sophorolipid-producing yeast in a submerged fermentation reactor to produce a yeast culture, said yeast culture comprising liquid fermentation medium, yeast cells and a mixture of hydrophobic SLP and hydrophilic SLP;

separating the hydrophobic and hydrophilic SLP by allowing the yeast culture to sit undisturbed at the end of the cultivation cycle in the fermentation reactor or in a first collection container for 12 to 50 hours, wherein a layer comprising hydrophobic SLP settles to the bottom of the yeast culture, and collecting the settled hydrophobic SLP layer into a second collection container, leaving behind a supernatant comprising dissolved hydrophilic SLP;

purifying the hydrophobic SLP and/or the hydrophilic SLP;

wherein the supernatant comprises hydrophilic SLP and glucose impurities dissolved therein, and wherein the method further comprises centrifuging the supernatant to remove cellular material and removing glucose impurities in the supernatant using a yeast digestion method and/or an enzymatic digestion method.

11. The method of claim 10, wherein the enzymatic digestion method comprises mixing glucose oxidase into the centrifuged supernatant to catalyze the conversion of glucose into gluconic acid and hydrogen peroxide; and, optionally, evaporating the hydrogen peroxide.

12. The method of claim 10, wherein the purified hydrophilic SLP has an HLB of 10 or greater.

* * * * *